US012668436B2

(12) United States Patent
Hirssig et al.

(10) Patent No.: US 12,668,436 B2
(45) Date of Patent: Jun. 30, 2026

(54) DEVICE AND PROCESS FOR THE AUTOMATED TRANSFER OF HOUSINGS

(71) Applicant: GAMBRO LUNDIA AB, Lund (SE)

(72) Inventors: Christian Hirssig, Burladingen (DE);
Maik Hanner, Bodelshausen (DE);
Pascal Maruhn, Burladingen (DE)

(73) Assignee: GAMBRO LUNDIA AB, Lund (SE)

( * ) Notice: Subject to any disclaimer, the term of this patent is extended or adjusted under 35 U.S.C. 154(b) by 68 days.

(21) Appl. No.: 18/724,679

(22) PCT Filed: Dec. 22, 2022

(86) PCT No.: PCT/EP2022/087451
§ 371 (c)(1),
(2) Date: Jun. 27, 2024

(87) PCT Pub. No.: WO2023/126301
PCT Pub. Date: Jul. 6, 2023

(65) Prior Publication Data
US 2025/0066142 A1 Feb. 27, 2025

(30) Foreign Application Priority Data

Dec. 28, 2021 (EP) .................................... 21217971

(51) Int. Cl.
*B65G 47/91* (2006.01)
*A61M 1/16* (2006.01)
*B01D 65/00* (2006.01)
*B65G 17/36* (2006.01)
(52) U.S. Cl.
CPC .......... *B65G 47/918* (2013.01); *B01D 65/00* (2013.01); *B65G 17/36* (2013.01); *A61M 1/16* (2013.01)

(58) Field of Classification Search
CPC ........ B01D 65/00; A61M 1/16; B65G 47/918; B65G 65/00; B65G 17/36; B65G 2207/08
USPC ........... 198/867.01, 867.08, 867.11, 803.11, 198/803.14
See application file for complete search history.

(56) References Cited

U.S. PATENT DOCUMENTS

| 316,172 | A | * | 4/1885 | Potts | ................. | B65G 2207/08 |
|---|---|---|---|---|---|---|
| 3,140,773 | A | * | 7/1964 | Cheh | ..................... | H01R 43/00 |
| | | | | | | 198/803.14 |
| 5,429,226 | A | * | 7/1995 | Ensch | .................... | B65G 17/44 |
| | | | | | | 198/803.14 |
| 5,984,085 | A | * | 11/1999 | Ponzio | .................. | H02K 15/00 |
| | | | | | | 198/345.3 |
| 7,584,837 | B2 | * | 9/2009 | Roether | .............. | B65G 17/002 |
| | | | | | | 198/470.1 |

(Continued)

FOREIGN PATENT DOCUMENTS

IT          20120070          8/2013

OTHER PUBLICATIONS

PCT Search Report and Written Opinion prepared for PCT Application No. PCT/EP2022/087451, completed Mar. 22, 2023.

(Continued)

*Primary Examiner* — James R Bidwell
(74) *Attorney, Agent, or Firm* — Barnes & Thornburg LLP

(57) ABSTRACT

The present disclosure relates to devices and processes for the automated transfer of tubular housings used for the manufacture of filtration and/or diffusion devices. e.g., capillary dialyzers or ultrafilters.

11 Claims, 1 Drawing Sheet

(56)    References Cited

U.S. PATENT DOCUMENTS

| | | | |
|---|---|---|---|
| 8,220,621 B2 * | 7/2012 | Koizumi | H01L 21/67333 |
| | | | 198/803.11 |
| 2002/0046925 A1 * | 4/2002 | Miyakawa | B28B 13/04 |
| | | | 198/465.1 |
| 2022/0162379 A1 * | 5/2022 | Li | C08G 65/2696 |

OTHER PUBLICATIONS

Alpha Plan Gmbh, "alphaFLOW® Pro—Wet Density Test & Drying—Filter / Dialyzer Assembly," 2021, https://www.youtube.com/watch?v=OmNRn-Ftpss.
Anonymous, "3D Printed End of Arm Tooling—Get Nylon Parts in Days Instead of Weeks," 2020, https://forerunner3d.com/3d-printed-end-of-arm-tooling/.

* cited by examiner a)                                          b)

DEVICE AND PROCESS FOR THE AUTOMATED TRANSFER OF HOUSINGS

CROSS-REFERENCE TO RELATED APPLICATIONS

This application is a national stage entry under 35 U.S.C. § 371 (b) of PCT International Application No. PCT/EP2022/087451, filed Dec. 22, 2022, which claims the benefit of European Patent Application Serial No. 21217971.7, filed Dec. 28, 2021, the entire disclosures of both of which are incorporated herein by reference.

TECHNICAL FIELD

The present disclosure relates to devices and processes for the automated transfer of tubular housings used for the manufacture of filtration and/or diffusion devices, e.g., capillary dialyzers or ultrafilters.

DESCRIPTION OF THE RELATED ART

The housings of filtration and/or diffusion devices like capillary dialyzers or ultrafilters are produced in an injection molding machine and placed into a box to transport them to several production lines. A box generally contains from about 320 to about 600 pieces. During transport, the housings may get displaced from their initial positions due to vibrations or centrifugal forces affecting the box. Especially the housings of the top layers in the box may shift from their position in any of the three directions in space. This fact makes it difficult to employ an automated device for removing the housings from the box and place them on a work piece tray. Therefore, the housings have to be handled manually by human workers. A worker has to take the displaced housings from the box and manually place them on a work piece tray for further processing. It would be desirable to automatize this step.

SUMMARY

The present disclosure provides devices and processes for the automated transfer of tubular housings used for the manufacture of filtration and/or diffusion devices from a storage box onto a work piece tray.

DETAILED DESCRIPTION

Figure 1:
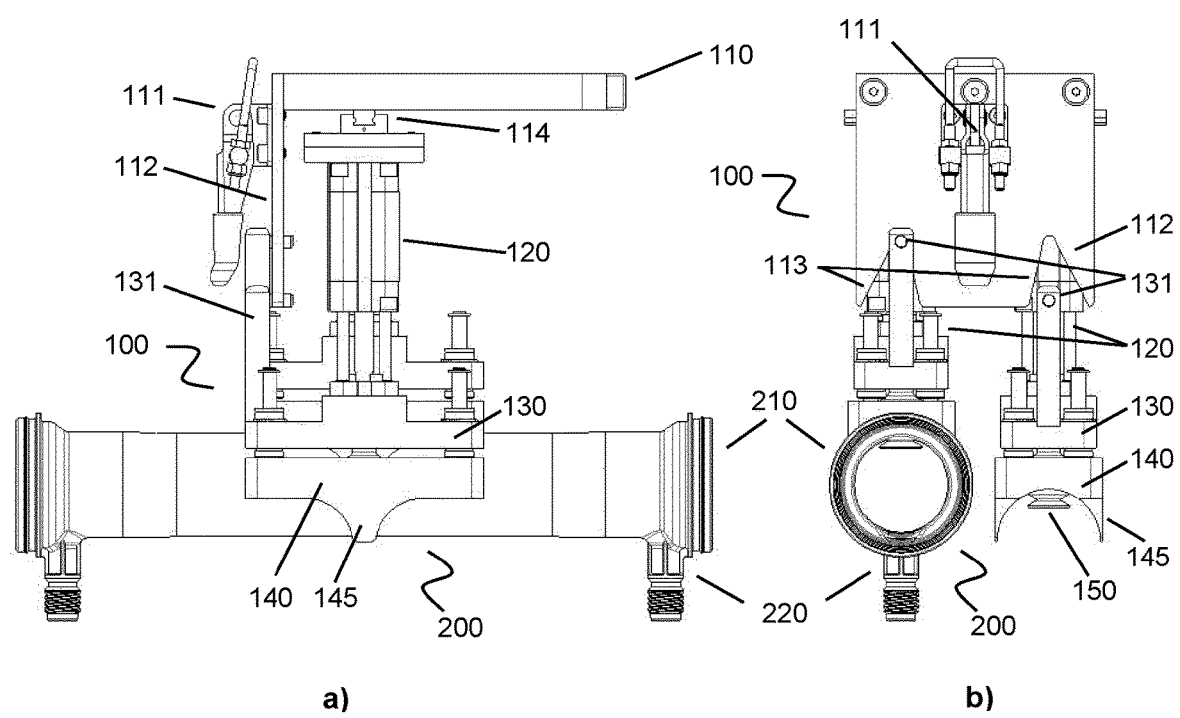
FIG. 1 shows a) a side view and b) a front view of an embodiment of a device of the present disclosure for transferring housings of filtration and/or diffusion devices from a storage box onto a work piece tray.

The present disclosure provides a device for the automated transfer of tubular housings used for the manufacture of filtration and/or diffusion devices, e.g., capillary dialyzers or ultrafilters, from a storage box onto a work piece tray (a "transfer device").

The transfer device comprises two receptacles for a tubular housing arranged in parallel. The receptacles are configured to move in a horizontal direction and a vertical direction independently from each other. The receptacles take the form of concave cylindrical half shells and each cylindrical half shell features a suction cup in its cavity.

In one embodiment of the transfer device, the receptacles take the form of concave cylindrical half shells with tapered protrusions extending from both longitudinal edges of the half shell. In one embodiment, the dimensions of the receptacle, i.e., the diameter of the cylindrical half shell, the length and curvature of the tapered protrusions, and the length of the receptacle, correspond to the dimensions of the tubular housings to be transferred by the transfer device. In one embodiment, the receptacles are interchangeable. This allows for using the same transfer device for transferring tubular housings of different dimensions.

Each cylindrical half shell features a suction cup in its cavity. In one embodiment, the suction cup is located in the center of the cylindrical half shell and extends into the cylindrical void defined by the cylindrical half shell. The suction cup is configured to aspirate a tubular housing and attach itself to the outer surface of the housing, fastening the housing in the cavity of the cylindrical half shell.

In one embodiment of the transfer device, both receptacles move horizontally on a rail which is perpendicular to the longitudinal axes of the receptacles.

In one embodiment of the transfer device, each receptacle is moved vertically by the piston of a pneumatic cylinder.

In one embodiment of the transfer device, the horizontal movement of the receptacles is limited depending on their vertical position.

In a particular embodiment, the transfer device comprises a base plate which allows for attaching the transfer device to a driving unit for moving the transfer device along the three spatial axes (x, y, and z). A locking mechanism affixes the transfer device to the driving unit. The locking mechanism is mounted on a front plate which is perpendicular to the base plate and attached to an edge of the base plate. A bottom edge of the front plate features two cutouts of roughly triangular form ("prisms"). In an embodiment of the transfer device, the altitude of the triangle of a cutout is about 20 mm, and the length of the baseline also is about 20 mm.

A rail running parallel to the front plate is mounted on the bottom surface of the base plate. Two pneumatic cylinders are attached to the rail and can freely move along the rail. A support is attached to the bottom end of the piston of each pneumatic cylinder. In an embodiment of the transfer device, the maximum displacement of the piston of each pneumatic cylinder is about 20 mm. A positioning finger is attached to the front end of each support, being perpendicular to the bottom surface of the support, and extending into one of the cutouts of the front plate located above the support. The edges of the cutout limit the lateral movement of the positioning finger and thereby the lateral movement of the support and the lateral movement of the attached pneumatic cylinder on the rail. The cutouts and the positioning fingers together limit the horizontal movement of the receptacles depending on their vertical position, i.e., depending on the extension of the piston of the corresponding pneumatic cylinder.

In one embodiment, the cutouts are asymmetric, and each of the positioning fingers can move farther towards the lateral edge of the front plate than towards the center axis of the front plate. In an embodiment of the transfer device, each of the positioning fingers has a maximum leeway of about 14 mm towards the lateral edge of the front plate, and about 6 mm towards the center axis of the front plate.

In one embodiment, a cylindrical half shell which extends into a central tapered protrusion ("finger") on each longitudinal side of the cylindrical half shell is mounted to each of the supports, each cylindrical half shell featuring a suction cup located in the center of the cylindrical half shell. The cylindrical half shells form the receptacles for the tubular housings.

The present disclosure also provides a work piece tray tubular housings of filtration and/or diffusion devices. The work piece tray comprises a base, a plurality of interchangeable holders for a tubular housing mounted on the base, and means for moving a tubular housing present in a holder along the longitudinal axis of the housing.

In one embodiment, eight holders are mounted on the base. In another embodiment, four holders are mounted on the base. Each holder is configured to hold a tubular housing of a filtration and/or diffusion device.

In one embodiment, the upper surface of each interchangeable holder takes the form of a concave cylindrical half shell and features at least one slot extending along the longitudinal axis of the half shell in the center of the half shell. In one embodiment, the curvature of the cylindrical half shell matches the dimensions of a header section of a tubular housing to be held in the holder, and the central slot receives fluid ports located on the outer wall of the housing.

In one embodiment of the work piece tray, the means for moving a tubular housing present in a holder along the longitudinal axis of the housing comprise at least one pneumatic cylinder. In one embodiment, each holder comprises a pneumatic cylinder. In another embodiment, pneumatic cylinders are located between two adjacent holders and are configured to move two housings present in the two adjacent holders. In still another embodiment, only one pneumatic cylinder is present, which moves a horizontal bar that displaces all housings present on the work piece tray. Any misalignment of the housings held in the plurality of holders is eliminated using the pneumatic cylinder(s) and the housings are moved to their target position on the work piece tray.

In one embodiment, the work piece tray additionally comprises means for moving each holder of the plurality of holders in a direction perpendicular to the longitudinal axis of the holder. The lateral distance of the housings in a storage box depends on the type of housing and generally is different to the desired lateral distance of the housings on a work piece tray. Therefore, the work piece tray comprises means for moving each holder of the plurality of holders in a direction perpendicular to the longitudinal axis of the holder. For loading the holders with housings, the holders are moved into positions where the lateral distance of two adjacent holders matches the lateral distance of the housings held in the transfer device. After all holders of the work piece tray have been loaded, the respective lateral distances of the holders on the base are adjusted to the desired final value for further processing the tubular housings.

In one embodiment, the work piece tray is mounted on a rail of a transport system which is configured to move the work piece tray between processing stations of a production line of filtration and/or diffusion devices. The work piece tray is driven by servo units of the transport system.

The present disclosure also provides a process for the automated transfer of tubular housings used for the manufacture of filtration and/or diffusion devices from a storage box onto a work piece tray. The process uses the transfer device of the present disclosure and comprises moving the transfer device over a storage box comprising tubular housings of filtration and/or diffusion devices, moving the device to coordinates corresponding to the positions of two housings in the storage box which have not been displaced from their initial position by first moving the transfer device over the housings to target x and y coordinates, and then descending the transfer device to the target z coordinate.

In one embodiment of the process, a driving unit moves the transfer device over a storage box comprising housings of filtration and/or diffusion devices. The driving unit moves the transfer device to coordinates corresponding to the positions of two housings in the storage box which have not been displaced from their initial position. The driving unit first moves the transfer device over the housings to the target x and y coordinates, and then slowly descends the transfer device to the target z coordinate.

In one embodiment of the process, both pneumatic cylinders of the transfer device are fully extended, i.e. their pistons are in their lowest position. The cylinders can freely move to both sides on a horizontal rail, taking along the receptacles. The lateral movement is limited by positioning fingers within cutouts of a front plate of the transfer device.

On lowering the transfer device to the target z coordinate, the receptacles of the transfer device engage the tubular housings. The tubular housings are fastened in the receptacles, and the receptacles subsequently are moved horizontally and/or vertically into a final position for transferring the tubular housings onto a work piece tray.

In one embodiment of the process, a tubular housing is first engaged by tapered protrusions of a receptacle and pulled into a cavity of the receptacle and fastened in the cavity by a suction cup located in the cavity. Each of the two suction cups of the transfer device attaches to the outer surface of one of the two housings at a position approximately halfway between the ends of the respective housing.

During the descent, the tapered protrusions of the receptacle contact the outer surface of the tubular housing and re-align it, if necessary. The suction cap contacts the outer surface of the cylindrical part of the tubular housing, aspiring it and pulling it into the cavity of the receptacle. Then the pistons of the pneumatic cylinders move up one by one, sliding the ends of the positioning fingers into the apices of the cutouts and bringing both housings into the correct position for transferring them onto a work piece tray.

In one embodiment, the transfer device is able to pick up two housings that have been displaced in the storage box from their initial position by up to 14 mm towards the outside of the box, or up to 6 mm towards the center of the box, as well as by up to 20 mm in height. Even tilted housings can be picked up from the storage box using the transfer device of the present disclosure.

In one embodiment, the process further comprises moving the transfer device over two adjacent holders for a tubular housing of the work piece tray of the present disclosure, and depositing the tubular housings in the holders of the work piece tray. When deposing the tubular housings in the holders, the fluid ports located on the outer wall of the housing are inserted into the central slots of the holders.

In one embodiment, the process further comprises aligning the ends of the tubular housings in the holders of the work piece tray. The tubular housings are aligned using the means for moving a tubular housing present in a holder along the longitudinal axis of the housing. Any misalignment of the housings held in the plurality of holders of the work piece tray is eliminated and the housings are moved to their target position on the work piece tray.

In one embodiment, the process further comprises adjusting the lateral distance of the holders on the work piece tray. In one embodiment of the process, the holders are moved into positions where the lateral distance of two adjacent holders matches the lateral distance of the housings held in the transfer device for loading the holders with housings.

The lateral distance of tubular housings in a storage box depends on the type of housing and generally is different to the desired lateral distance of the housings on a work piece tray. In one embodiment, the process therefore further comprises adjusting the lateral distance of the holders on the work piece tray to a desired final value for further processing the tubular housings after all holders mounted on the work piece tray have been loaded.

Exemplary embodiments of the device and the process of the present disclosure are further described hereafter with reference to the drawings. Throughout the figures, the same reference signs are used to refer to similar features.

It will be understood that the features mentioned above and those described hereinafter can be used not only in the combination specified but also in other combinations or on their own, without departing from the scope of the present invention.

DETAILED DESCRIPTION OF THE DRAWINGS

FIG. 1 shows a) a side view and b) a front view of an embodiment of a device 100 of the present disclosure for transferring housings 200 of filtration and/or diffusion devices from a storage box onto a work piece tray 300.

The transfer device 100 comprises a base plate 110 which allows for attaching the transfer device 100 to a driving unit for moving the transfer device 100 to a driving unit for moving the transfer device 100 along the three spatial axes (x, y, and z). A locking mechanism 111 affixes the transfer device to the driving unit. The locking mechanism 111 is mounted on a front plate 112 which is perpendicular to the base plate [111] 110 and attached to an edge of the base plate 110. A bottom edge of the front plate 112 features two cutouts 113 of roughly triangular form ("prisms"). In an embodiment of the transfer device 100, the altitude of the triangle of a cutout 113 is about 20 mm, and the length of the baseline also is about 20 mm. A rail 114 running parallel to the front plate 110. Two pneumatic cylinders 120 are attached to the rail 114 and can freely move along the rail 114. A support 130 is attached to the bottom end of the piston of each pneumatic cylinder 120. In an embodiment of the transfer device 100, the maximum displacement of the piston of each pneumatic cylinder 120 is about 20 mm. A positioning finger 131 is attached to the front end of each support 130, and extending into one of the cutouts 113 of the front plate 112 located above the support 130. The edges of the cutout 113 limit the lateral movement of the positioning finger 131 and thereby the lateral movement of the support 130 and the lateral movement of the attached pneumatic cylinder 120 on the rail 114. As shown in the drawing, the cutouts 113 are asymmetric, and each of the positioning fingers 131 can move farther towards the lateral edge of the front plate 112 than towards the center axis of the front plate 112. In an embodiment of the transfer device 100, each of the positioning fingers 131 has a maximum leeway of about 14 mm towards the lateral edge of the front plate 112, and about 6 mm towards the center axis of the front plate 112. A cylindrical half shall 140 which extends into a central projection 145 ("finger") on each longitudinal side of the cylindrical half shell 140 is mounted to each of the supports 130. Each cylindrical half shell 140 features a suction cup 150 located in the center of the cylindrical half shell 140 and extending into the cylindrical void defined by the cylindrical half shell 140. The suction cup 150 is configured to aspirate a housing 200 and attached itself to the outer surface of the housing 200, fastening the housing 200 in the cavity of the cylindrical half shell 140, as shown in the drawings.

In the process of the present disclosure, a driving unit moves the transfer device 100 over a storage box comprising housings 200 of filtration and/or diffusion devices. The driving unit moves the transfer device 100 to coordinates corresponding to the positions of two housings 200 in the storage box which have not been displaced from their initial position, so that each of the two suction cups 150 of the transfer device 100 would touch the outer surface of one of the two housings 200 halfway between the ends of the respective housing 200. The driving unit first moves the transfer device 100 over the housings 200 to the target x and y coordinates, and then slowly descends the transfer device 100 to the target z coordinate. Both pneumatic cylinders 120 of the transfer device 100 are fully extended, i.e. their pistons are in their lowest position. The cylinders 120 can freely move to both sides on the rail 114, taking along the cylindrical half shells 140. The lateral movement is limited by the positioning fingers 131 within the cutouts 113. During the descent, the projections 145 of the cylindrical half shell 140 contact the outer surface of the housing 200 and re-align it, if necessary. The suction cup 150 contacts the outer surface of the cylindrical part of the housing 200, aspiring it and pulling it into the cavity formed by the cylindrical half shell 140. Then the pistons of the pneumatic cylinders 120 move up one by one, sliding the ends of the positioning fingers 131 into the pieces of the cutouts 113 and bringing both housings 200 into the correct position for transferring them onto a work piece tray 300. In one embodiment, the transfer device 100 is able to pick up two housings 200 that have been displaced in the storage box from their initial position by up to 14 mm towards the outside of the box, or up to 6 mm towards the center of the box, as well as by up to 20 mm in height. Even tilted housings can be picked up from the storage box.

Figure 2:
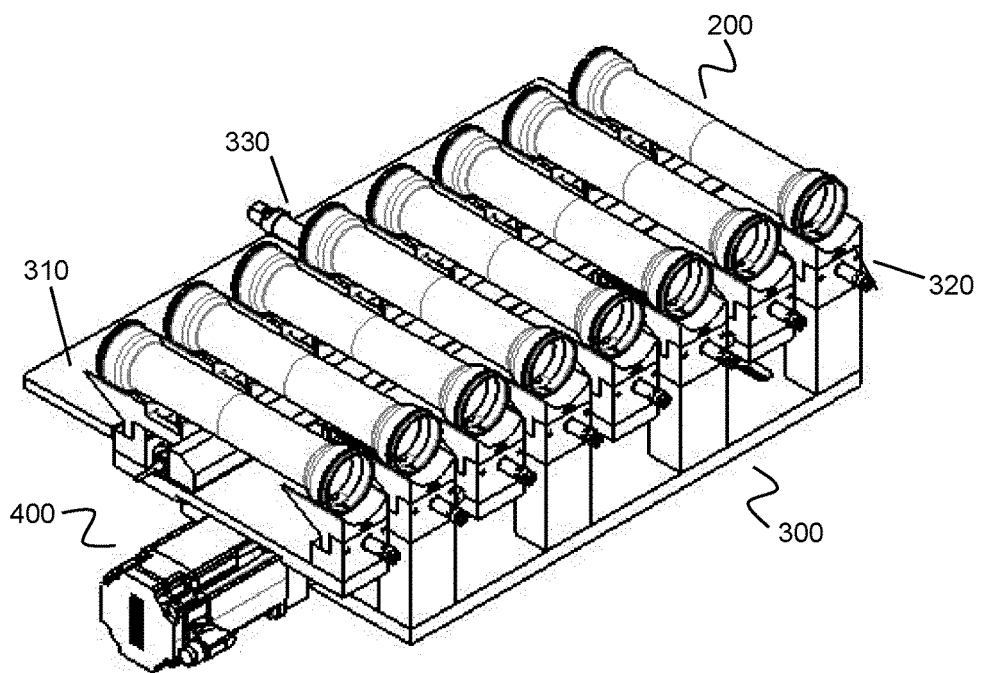
FIG. 2 shows a perspective view of an embodiment of a work piece tray of the present disclosure carrying a plurality of housings of filtration and/or diffusion devices.

FIG. 2 shows a perspective view of an embodiment of a work piece tray 300 of the present disclosure carrying a plurality of housings 200 of filtration and/or diffusion devices and mounted on a transport system 400.

The work piece tray 300 comprises a base 310 which is mounted on a rail of a transport system 400 and driven by servo units of the transport system 400. A plurality of interchangeable holders 320 is mounted on the base 310. In the embodiment shown, eight holders 320 are mounted on the base 310. In another embodiment, four holders 320 are mounted on a base 310. Each holder 320 is configured to hold a housing 200 of a filtration and/or diffusion device. The top surface of each holder 320 forms a (concave) cylindrical half shell and has at least one central slit in the cylindrical half shell running in longitudinal direction of the holder 320. The curvature of the cylindrical half shell matches the dimensions of the header section 210 of the housing 200 to be held in the holder 320, and the central slit receives the fluid ports 220 located on the outer wall of the housing 200. At least one pneumatic cylinder 330 is present in the work piece tray 300 and is configured to move a housing 200 present in a holder 320 along its longitudinal axis. In one embodiment, each holder 320 comprises a pneumatic cylinder 330. In another embodiment, pneumatic cylinders 330 are located between two adjacent holders 320 and are configured to move two housings 200 present in the two adjacent holders 320. In still another embodiment, only one pneumatic cylinder 330 is present, which moves a horizontal bar that displaces all housings 200 present on the work piece tray 300. Any misalignment of the housings 200 held in the plurality of holders 320 is eliminated using the pneumatic cylinder(s) 330 and the housings are moved to their target position on the work piece tray 300.

The lateral distance of the housings 200 in the storage box depends on the type of housing and generally is different to the desired lateral distance of the housings 200 on a work piece tray 300. Therefore, the work piece tray 300 in one embodiment comprises a distancer (not shown). The distancer moves the holders 320 of the work piece tray 300 in a direction perpendicular to their longitudinal axis. For loading the holders 320 with housings 200, the distancer moves the holders 320 into positions where the lateral distance of two holders 320 matches the lateral distance of the housings 200 held in the transfer device 100. After all holders 320 of the work piece tray 300 have been loaded, the distancer adjusts the respective lateral distances of the holders 320 on the base 310 to the desired value.

LIST OF REFERENCE SIGNS

100 transfer device
110 base plate
111 lock mechanism
112 front plate
113 cutout ("prism")
114 rail
120 pneumatic cylinder
130 support
131 positioning finger
140 half shell
145 protrusion ("finger")
150 suction cup
200 tubular housing
210 header section
220 fluid port
300 work piece tray
310 base
320 holder
330 pneumatic cylinder
400 transport system

The invention claimed is:

1. A device for the automated transfer of tubular housings of filtration and/or diffusion devices from a storage box onto a work piece tray, characterized in that the device comprises two receptacles for a tubular housing arranged in parallel, the receptacles taking the form of concave cylindrical half shells, each cylindrical half shell featuring a suction cup in its cavity, and the receptacles being configured to independently from each other move in a horizontal direction and a vertical direction.

2. The device of claim 1, wherein the receptacles take the form of concave cylindrical half shells with tapered protrusions extending from both longitudinal edges of the half shell.

3. The device of claim 1, wherein both receptacles move horizontally on a rail which is perpendicular to the longitudinal axes of the receptacles.

4. The device of claim 1, wherein each receptacle is moved vertically by a piston of a pneumatic cylinder.

5. The device of claim 1, wherein the horizontal movement of the receptacles is limited depending on their vertical position.

6. A work piece tray for tubular housings of filtration and/or diffusion devices comprising a base, characterized in that the work piece tray comprises a plurality of interchangeable holders for a tubular housing mounted on the base, and means for moving a tubular housing present in a holder along the longitudinal axis of the housing, wherein an upper surface of each interchangeable holder takes the form of a concave cylindrical half shell and features at least one slot extending along the longitudinal axis of the half shell in the center of the half shell.

7. The work piece tray of claim 6, additionally comprising means for moving each holder of the plurality of holders in a direction perpendicular to the longitudinal axis of the holder.

8. A process for the automated transfer of tubular housings of filtration and/or diffusion devices from a storage box onto a work piece tray, the process comprising moving the device of claim 1 over a storage box comprising tubular housings of filtration and/or diffusion devices, moving the device to coordinates corresponding to the positions of two housings in the storage box which have not been displaced from their initial position by first moving the transfer device over the housings to target x and y coordinates, and then descending the transfer device to the target z coordinate, thereby allowing the receptacles of the device to engage a tubular housings, fastening the tubular housings in the receptacles, and moving the receptacles horizontally and/or vertically into a final position for transferring the housings onto a work piece tray.

9. The process of claim 8, wherein a tubular housing is first engaged by tapered protrusions of a receptacle and pulled into a cavity of the receptacle and fastened in the cavity by a suction cup located in the cavity.

10. The process of claim 8, further comprising moving the device over two adjacent holders for a tubular housing of the work piece tray of claim 6, and deposing the tubular housings in the holders of the work piece tray.

11. The process of claim 10, further comprising aligning the ends of the tubular housings in the holders of the work piece tray.

* * * * *